US011589877B2

United States Patent
Duerr

(10) Patent No.: US 11,589,877 B2
(45) Date of Patent: Feb. 28, 2023

(54) WEDGE OSTEOTOMY DEVICE AND METHOD OF USE

(71) Applicant: Colorado State University Research Foundation, Fort Collins, CO (US)

(72) Inventor: Felix Duerr, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 459 days.

(21) Appl. No.: 16/596,395

(22) Filed: Oct. 8, 2019

(65) Prior Publication Data

US 2020/0113581 A1    Apr. 16, 2020

Related U.S. Application Data

(60) Provisional application No. 62/743,992, filed on Oct. 10, 2018.

(51) Int. Cl.
*A61B 17/15*    (2006.01)
*A61B 90/00*    (2016.01)

(52) U.S. Cl.
CPC ..... *A61B 17/152* (2013.01); *A61B 2090/0811* (2016.02); *A61B 2090/08021* (2016.02)

(58) Field of Classification Search
CPC ..... A61B 17/15; A61B 17/151; A61B 17/152; A61B 2090/08021; A61B 2090/0811
See application file for complete search history.

(56) References Cited

U.S. PATENT DOCUMENTS

| | | | |
|---|---|---|---|
| 4,703,751 A | 11/1987 | Pohl | |
| 5,275,603 A | 1/1994 | Ferrante et al. | |
| 5,364,401 A | 11/1994 | Ferrante et al. | |
| 5,413,579 A | 5/1995 | Tom du Toit | |
| 5,484,446 A | 1/1996 | Burke et al. | |
| 5,810,827 A * | 9/1998 | Haines | A61B 17/1764 606/88 |
| 2002/0165552 A1* | 11/2002 | Duffner | A61B 17/152 606/87 |
| 2004/0106926 A1* | 6/2004 | Leitner | A61B 17/152 606/87 |
| 2005/0070909 A1 | 3/2005 | Egger et al. | |
| 2005/0273112 A1* | 12/2005 | McNamara | A61B 17/152 606/87 |
| 2007/0265634 A1* | 11/2007 | Weinstein | A61B 17/15 606/87 |

(Continued)

OTHER PUBLICATIONS

International Search Report and Written Opinion, PCT/US2019/055209, dated Dec. 12, 2019.

*Primary Examiner* — Kevin T Truong
*Assistant Examiner* — Diana Jones
(74) *Attorney, Agent, or Firm* — Polsinelli PC

(57) ABSTRACT

A wedge osteotomy device including a cutting guide coupled to a base plate via a joint. The cutting guide configured to pivot relative to the base plate about a pivot axis extending through the joint. The cutting guide including a guide body including a cutting slot extending through the guide body, an arcuate slot extending through the guide body and defining a radius to the joint, and a plurality of markers on the guide body identifying a position of the cutting guide relative to the base plate. The base plate including planar top and bottom surfaces.

20 Claims, 13 Drawing Sheets

(56) References Cited

U.S. PATENT DOCUMENTS

| | | | | |
|---|---|---|---|---|
| 2008/0195099 A1* | 8/2008 | Minas | ............... | A61B 17/8061 |
| | | | | 606/88 |
| 2008/0262500 A1* | 10/2008 | Collazo | ............. | A61B 17/8095 |
| | | | | 606/88 |
| 2010/0087824 A1* | 4/2010 | Collazo | ............... | A61B 17/151 |
| | | | | 606/88 |
| 2012/0130383 A1* | 5/2012 | Budoff | ............... | A61B 17/8866 |
| | | | | 606/87 |

* cited by examiner

WEDGE OSTEOTOMY DEVICE AND METHOD OF USE

CROSS-REFERENCE TO RELATED APPLICATION

This application claims the benefit of U.S. Provisional Application No. 62/743,992, filed Oct. 10, 2018, which is hereby incorporated by reference in its entirety into the present application.

TECHNICAL FIELD

Aspects of the present disclosure involve a wedge osteotomy device, and, in particular, a closing wedge osteotomy device for the correction of limb deformities and certain ligament diseases.

BACKGROUND

An osteotomy is a surgical procedure where a bone is cut to shorten, lengthen, straighten it, or to change its alignment for other biomechanical reasons. One particular type of osteotomy is a wedge osteotomy that can be broken down into two types: opening wedge osteotomies; and closing wedge osteotomies. An opening wedge osteotomy is where a bone is cut (e.g., via a simple transverse osteotomy) and the bone is pivoted "open". Then, bone graft is added to the open wedge-space along with a bone plate, for example. For this procedure, the angle can be adjusted intra-operatively since it is accepted that there will be a gap between the two fracture ends. A closing wedge osteotomy, on the other hand, is where a bone is cut twice and a wedge of bone is removed (i.e. at an angle relative to the first cut). The two osteotomies result in the removal of a bone "wedge" of a specific angle as determined pre-operatively. The remaining portions of the bone are "closed", and a secured together with a plate, for example. For this procedure, one of the goals is to allow compression of both bone ends, which is why the angle of the wedge has to be accurate.

Wedge osteotomies are commonly performed for the treatment of osseous deformities in humans and animals (e.g., dogs). As an example, closing wedge osteotomies in veterinary medicine may be performed for correction of deformities such as femoral varus (distal femoral osteotomy), cranial cruciate ligament disease (cranial closing wedge osteotomy) and angular limb deformity correction. Another indication is the treatment of various joint conditions that may benefit from a change of the axial alignment of the adjacent bones (load-shifting procedures). Currently, wedge osteotomies are planned by calculating the desired angle of the wedge and the surgeon attempts to perform two bone cuts (a transverse osteotomy, and a wedge-resection at an angle relative to the transverse osteotomy) that are executed with the following goals: First, the degree of the wedge should represent the desired amount based on pre-operative planning. Second, the two osteotomies should be parallel to each other (i.e. after reduction of the wedge there should be no shift of the axes in the 'non-corrected' planes). That is, the planes defined by the osteotomies should not intersect with each other. Third, the osteotomies should meet exactly at the "tip" of the wedge (i.e. a wedge is removed rather than a trapezoid piece of bone, which results in additional, undesirable limb shortening).

With these thoughts in mind, among others, aspects of the wedge osteotomy device and method of use, disclosed herein, were conceived.

BRIEF SUMMARY

Aspects of the present disclosure may include a wedge osteotomy device may include a cutting guide and a base plate coupled to each other via a joint. The cutting guide may be configured to pivot relative to the base plate about a pivot axis extending through the joint. The cutting guide may include a guide body including a cutting slot extending through the guide body, an arcuate slot extending through the guide body and defining a radius to the joint, and a plurality of markers on the guide body identifying a position of the cutting guide relative to the base plate. The base plate may include planar top and bottom surfaces.

In certain instance, the device may include a blade guard coupled to the base plate and may include a surface perpendicular to the planar top surface.

In certain instance, the pivot axis is at the intersection of the surface of the blade guard and the planar top surface of the base plate.

In certain instance, the cutting slot is a planar cutting slot.

In certain instance, the position is an angular position.

In certain instance, the guide body further includes a cylindrical bore defining a first portion of the joint and extending through the guide body, the cutting slot intersecting the cylindrical bore.

In certain instance, the base plate further may include a shaft extending from a side surface of the base plate, the shaft being receivable within the cylindrical bore and defining a second portion of the joint.

In certain instance, the shaft may include a partial cylinder having an opened segment extending longitudinally on the shaft, the partial cylinder including a planar first surface coplanar with the planar top surface of the base plate.

In certain instance, the partial cylinder may include a planar second surface perpendicular to the planar first surface.

In certain instance, the cutting slot intersects the pivot axis.

In certain instance, the device may include a thumb-screw securable to the base plate through the arcuate slot.

In certain instance, the guide body further includes at least one anchor bores extending through the guide body, the at least one anchor bores positioned below the cutting slot.

Aspects of the present disclosure may include a wedge osteotomy device may include a cutting guide coupled to a base plate via a joint. The cutting guide may be configured to pivot relative to the base plate about a pivot axis extending through the joint. The cutting guide may include a guide body including a cutting slot extending through the guide body, and a bore extending through the guide body and intersecting the cutting slot. The base plate may include planar top and bottom surfaces and a shaft extending from a side thereof. The shaft may be receivable within the bore to form the joint. The shaft may include a partial cylindrical outer surface, and a side opening extending from the partial cylindrical outer surface to a central axis thereof.

In certain instance, the device may include a thumb-screw rotatably coupled with the guide body and configured to secure the cutting guide in an angular position relative to the base plate.

In certain instance, the shaft further may include a planar surface coplanar with the planar top surface of the base plate.

In certain instance, the cutting slot extends to the pivot axis through the side opening of the shaft of the base plate.

Aspects of the present disclosure may include a method of performing a closing wedge osteotomy on a bone having a transverse osteotomy exposing a distal bone surface on a proximal portion of the bone and a proximal bone surface on a distal portion of the bone. The method may include positioning a bottom surface of a base plate of a wedge osteotomy device on the proximal bone surface of the distal portion of the bone and positioning a top surface of the base plate on the distal bone surface of the proximal portion of the bone. The wedge osteotomy device may include a cutting guide pivotally coupled to the base plate via a joint. The cutting guide may include a guide body including a cutting slot extending there through, at least one anchor bore extending there through, and a lock configured to secure the cutting guide in an angular position relative to the base plate. The method may further include setting an angular orientation of the cutting guide relative to the base plate for a desired cut to the proximal portion of the bone. The method may further include actuating the lock, delivering an anchor through the at least one anchor bore and into the proximal portion of the bone, and inserting a cutting tool through the cutting slot and cutting the proximal portion of the bone.

In certain instance, the guide body further includes an arcuate slot extending through the guide body and defining a radius to the joint, and a plurality of markers on the guide body identifying a position of the cutting guide relative to the base plate.

In certain instance, the base plate may further include a shaft extending from a side thereof, and wherein the guide body further may include a bore opening configured to receive the shaft therein, the shaft and the bore opening forming the joint.

In certain instance, the bore opening and the cutting slot intersect each other, and the shaft has a longitudinal opening therein for the cutting tool to extend therein when the cutting tool is used to cut the proximal portion of the bone.

BRIEF DESCRIPTION OF THE DRAWINGS

Example embodiments are illustrated in referenced figures of the drawings. It is intended that the embodiments and figures disclosed herein are to be considered illustrative rather than limiting.

DETAILED DESCRIPTION

I. Wedge Osteotomy Device

A. Overview

Figure 1A:
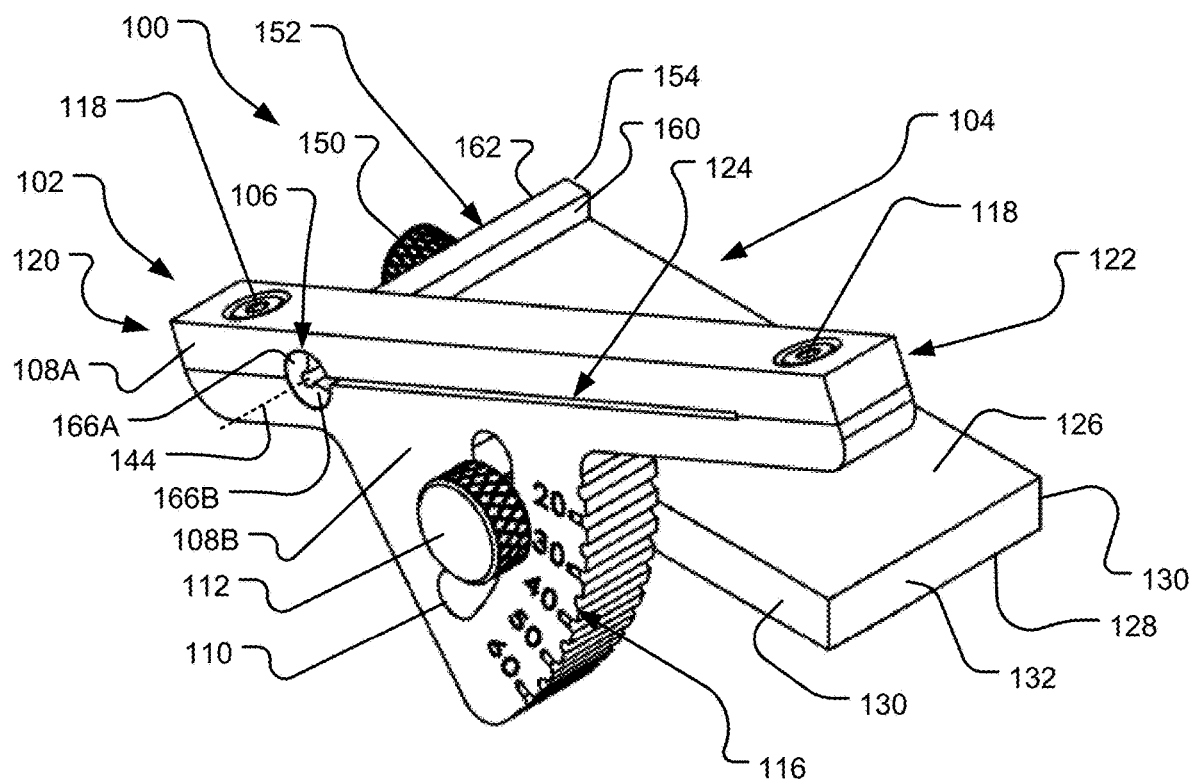
FIG. 1A is an isometric view of a wedge osteotomy device in a first instance.
Figure 1B:
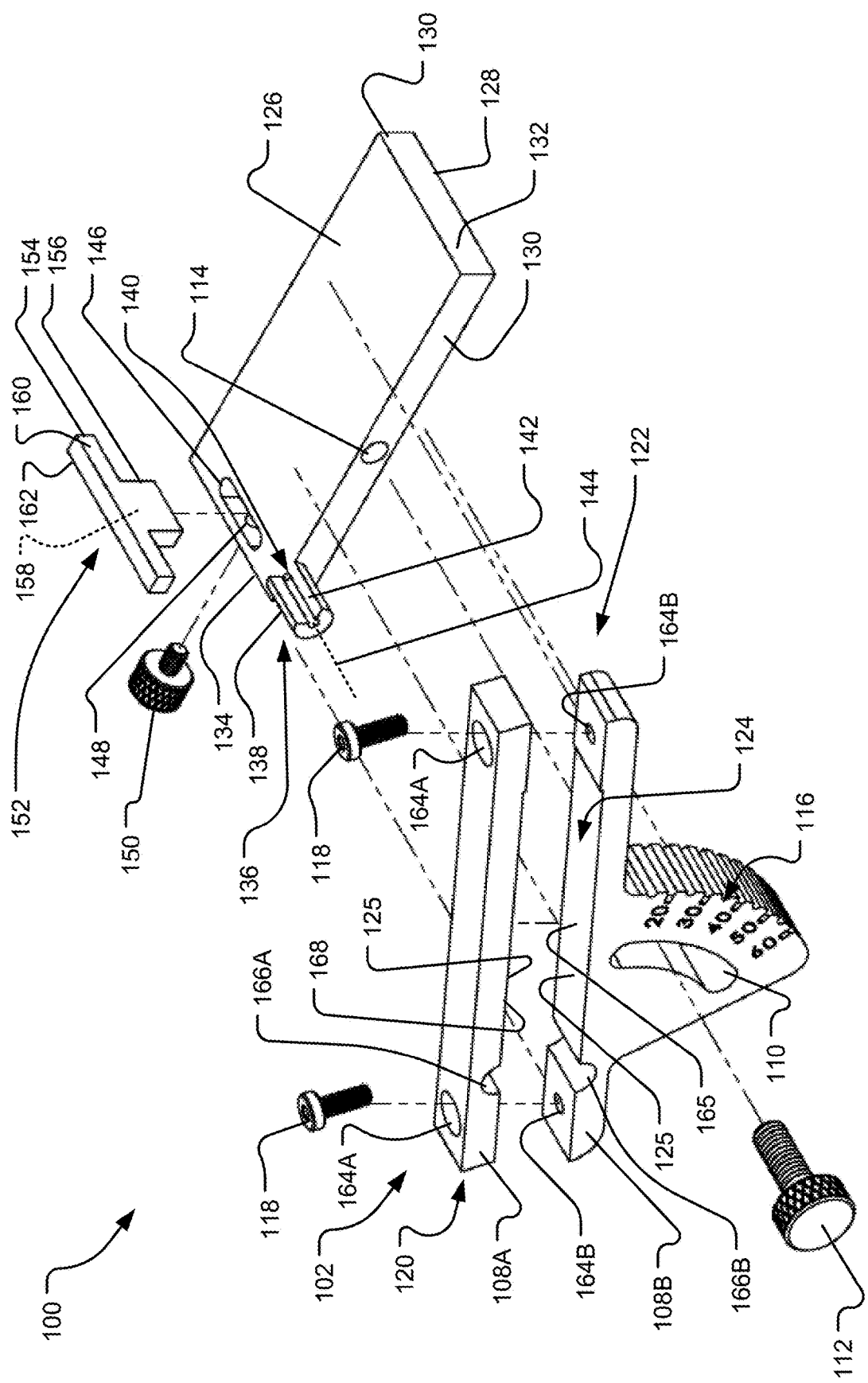
FIG. 1B is an isometric exploded view of the wedge osteotomy device.
Figure 1C:
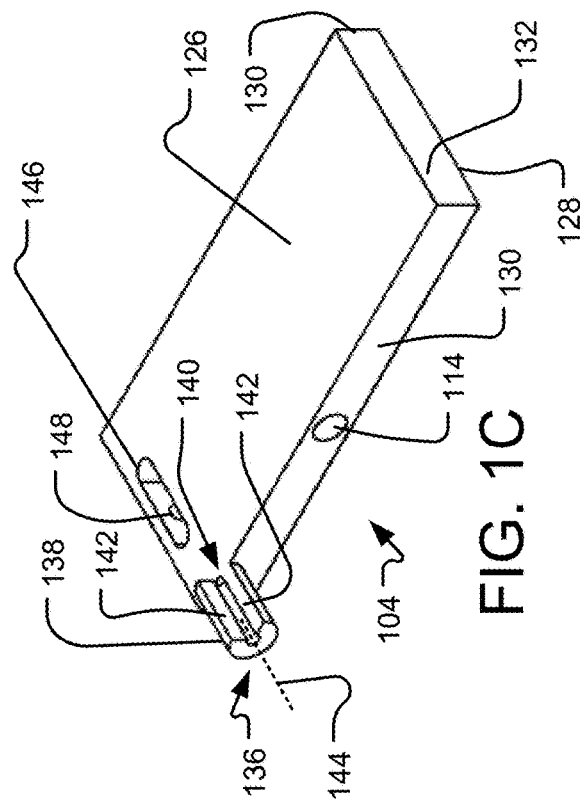
FIGS. 1C-1F are, respectively, an isometric view, a top view, a side view, and a front view of a base plate of the wedge osteotomy device.

Aspects of the present disclosure involves a wedge osteotomy device 100 as seen in FIG. 1A, which shows the device in an isometric view. As seen in the figure, the device 100 may include a cutting guide 102 and a base plate 104 that are pivotally connected at a joint 106. The cutting guide 102 may include a guide body 108 that may be manufactured from a single component or multiple components. FIG. 1B, which is an isometric exploded view of the wedge osteotomy device 100, depicts an upper guide body 108A and a lower guide body 108B in a sample construction; however, the device 100 may be constructed of a single guide body 108 without departing from the teachings of the present disclosure.

As seen in FIGS. 1A and 1B, the lower guide body 108B of the wedge osteotomy device 100 may include an arcuate slot 110 with an arc defined by a radius to the joint 106. A thumb-screw 112 may extend through the arcuate slot 110 and into a threaded bore 114 extending into a side surface of the base plate 104. The thumb-screw 112 may be tightened against the guide body 108 to secure an angular orientation of the base plate 104 relative to the cutting guide 102. The thumb-screw 112 may also be loosened so as to permit the base plate 104 to freely rotate relative to the cutting guide 102 about the joint 106.

Adjacent the arcuate slot 110 are a series of markers 116 identifying an angular orientation of the cutting guide 102 relative to the base plate 104. The series of markers 116 may include numerical markings indicating the angular orientation in degrees (e.g., 20 degrees, 30 degrees, 40 degrees, 50 degrees, 60 degrees), and/or the series of markers 116 may include notches defined on a front surface of the cutting guide 102.

As seen in FIG. 1B, the upper and lower guide bodies 108A, 108B may be secured together via a pair of threaded members 118. The pair of threaded members 118 may couple the guide bodies 108A, 108B together on opposite sides of the joint 106 with one near a back side 120 of the guide body 108 and one near the front side 122 of the guide body 108.

As seen in FIGS. 1A-1B, a cutting slot 124 is defined between the upper and lower guide bodies 108A, 108B. The guide slot 124 includes planar guiding surfaces 125 for guiding a cutting tool (not shown) in making osteotomies to the bone there through. The cutting slot 124 may be partially defined within each of the upper and lower guide bodies 108A, 108B, as seen in the figures, or may be defined within one of the upper and lower guide bodies 108A, 108B only.

B. Base Plate

Reference is made to FIGS. 1C-1F, which depict, respectively, an isometric view, a top view, a side view, and a front view of the base plate 104. As seen in the figures, the base plate 104 may include a top surface 126 that may be planar, a bottom surface 128 that may be planar, side surfaces 130, a front surface 132, and a back surface 134. A shaft 136 forming a first part of the joint 106 may extend outward from one of the side surfaces 130 near the back surface 134. As seen in the figures, the shaft 136 may include a partial cylindrical surface 138 (the partial cylindrical outer surface of a hollow cylinder) with an opening 140 (i.e., ninety degree segment in the shape of a pie) extending longitudinally down the shaft 136. The shaft 136 includes a pair of planar inner surfaces 142 defined by the opening 140. One of the pair of surfaces 142 is coplanar with the top surface 126 of the base plate 104 and the other of the pair of surfaces 142 is perpendicular to the other surface 142 and the top surface 126 of the base plate 104.

Figure 1F:
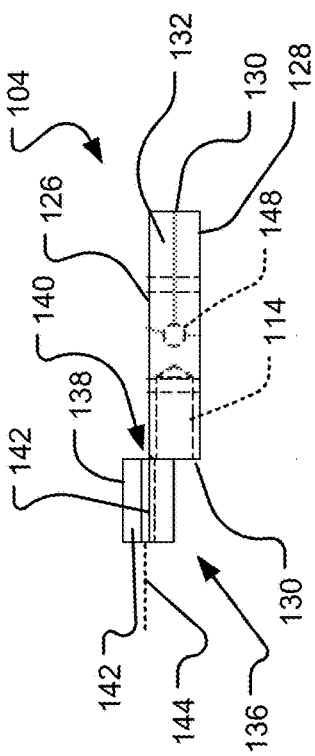
Figure 1D:
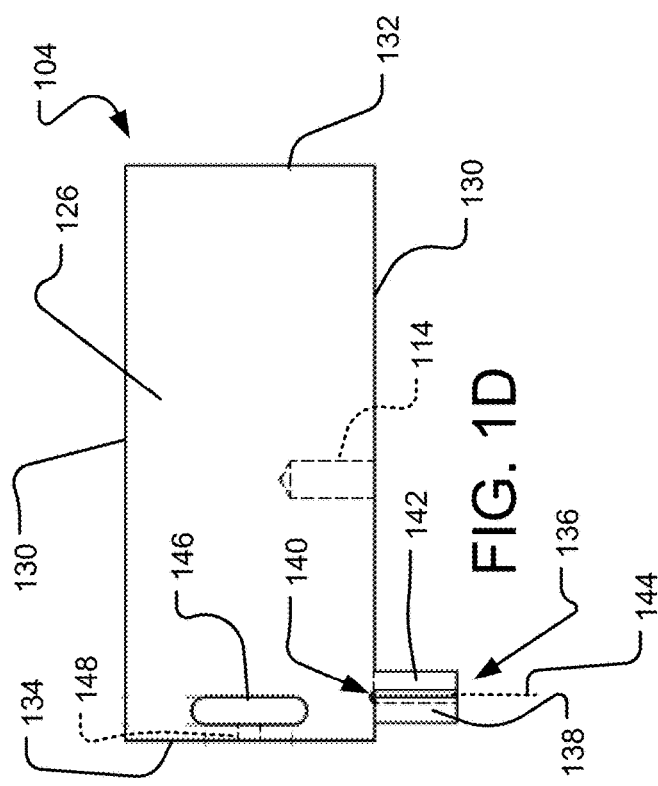
Figure 1E:
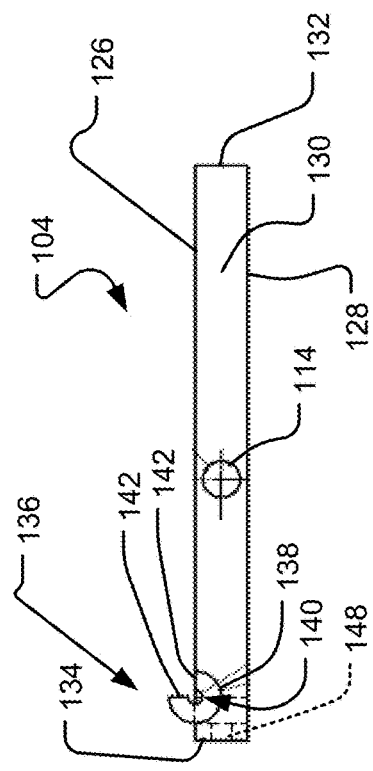

As seen in FIG. 1E, the opening 140 in the shaft 136 extends to the central axis 144 (otherwise known as the pivot axis) of the shaft 136 where there is a cylindrical bore down the central axis 144 of the shaft 136. The central axis 144 is coplanar with the top surface 126 of the base plate 104. As best seen in FIGS. 1E and 1F, a portion of the shaft 136 extends above the top surface 126 of the base plate 104. As the cutting guide 102 rotates relative to the base plate 104 about the joint 106, the cutting guide 102 rotates about the central axis 144 of the shaft 136.

As seen in the figures, a blade guard opening 146 is formed through the top surface 126 to the bottom surface 128 of the base plate 104 near the back surface 134. A bore 148 extends through the back surface 134 into the blade guard opening 146. The bore 148 may be threaded so as to receive a thumb-screw 150 (shown in FIG. 1B). The blade guard opening 146 is sized to receive a blade guard 152, which is shown in FIGS. 1G-1J, which are, respectively, an isometric view, a top view, a front view, and a side view.

C. Blade Guard

Figure 1G:
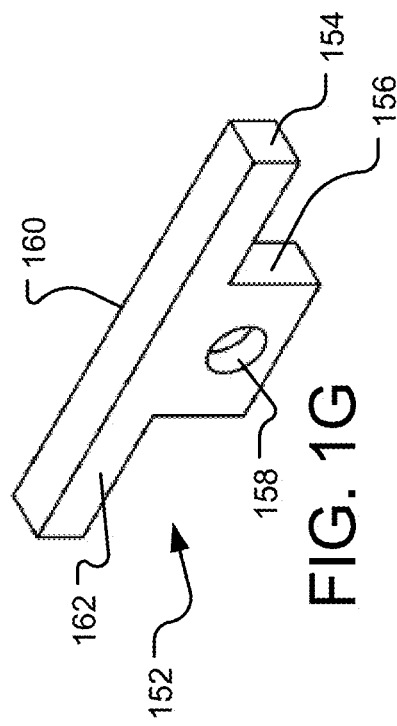
FIGS. 1G-1J are, respectively, an isometric view, a top view, a front view, and a side view of a blade guard of the wedge osteotomy device.
Figure 1J:
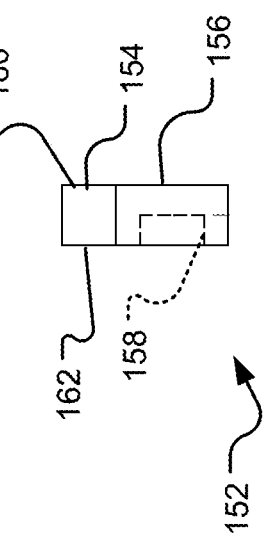
Figure 1H:
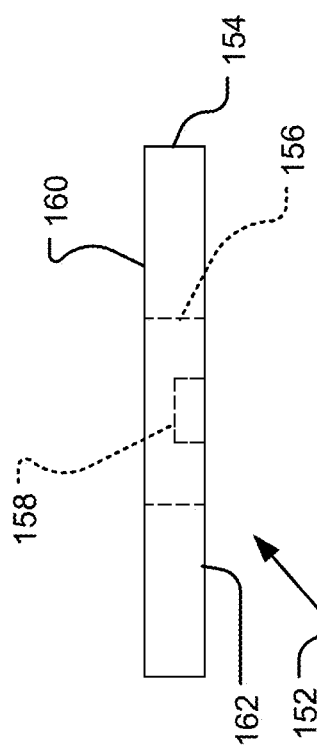
Figure 1I:
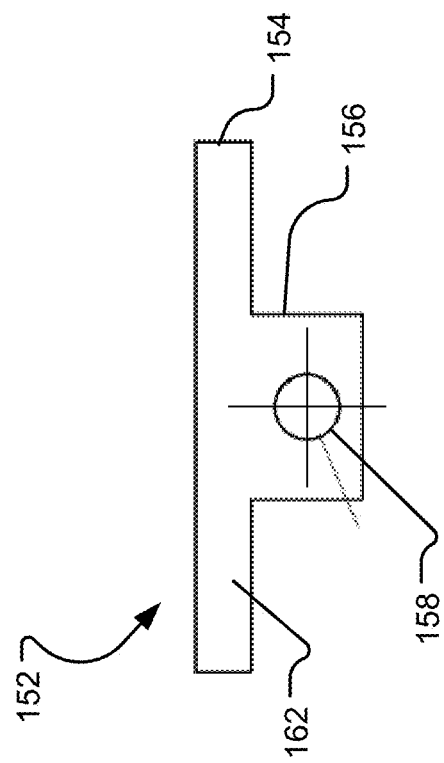

As seen in FIGS. 1G and 1I, the blade guard 152 is T-shaped and may include a guard member 154 and a tab 156 with a partial-bore or indentation 158 extending partially there through. The tab 156 may be received within the blade guard opening 146, and the thumb-screw 150 (shown in FIG. 1B) may be received through the bore 148 of the base plate 104 and into the indentation 158 of the blade guard 152 to secure the blade guard to the base plate 104. Alternatively, the partial bore 158 may be a through-hole without departing from the teachings of the present disclosure.

The blade guard 152 may include a front surface 160 and a back surface 162, both of which may be planar. When the blade guard 152 is secured or otherwise coupled to the base plate 104, the front surface 160 may be perpendicular to the top surface 126 of the base plate 104, as seen in FIG. 1A. And, the front surface 160 of the blade guard 152 is also coplanar with the vertical surface 142 of the shaft 136. Additionally, the axis of intersection of the front surface 160 and the top surface 126 of the base plate 104 is collinear with central axis 144 of the shaft 136. Together, the front surface 160 of the blade guard 152 and the vertical surface 142 of the shaft 136 form a stop for a cutting blade.

While the blade guard 152 is depicted as a separate component from the base plate 104, the blade guard 152 may be a unitary component of the base plate 104. That is, the base plate 104 may be unitarily formed with the blade guard 152.

D. Cutting Guide

Figure 1K:
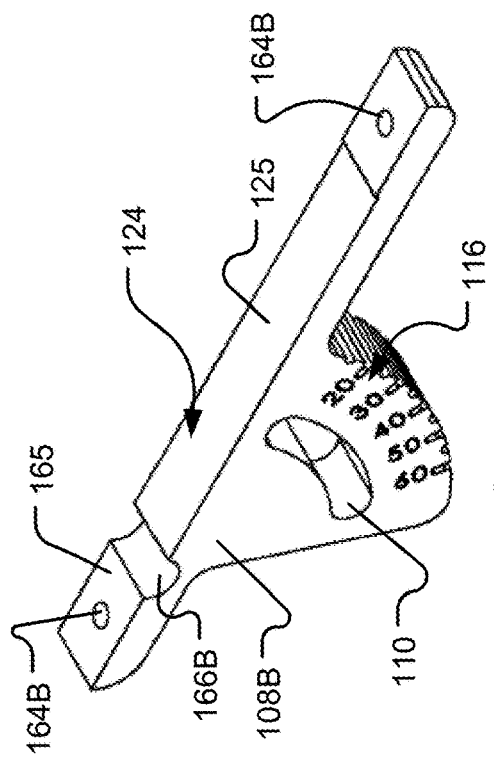
FIGS. 1K-1M are, respectively, an isometric view, a top view, and a side view of the lower part of the cutting guide of the wedge osteotomy device.
Figure 1L:
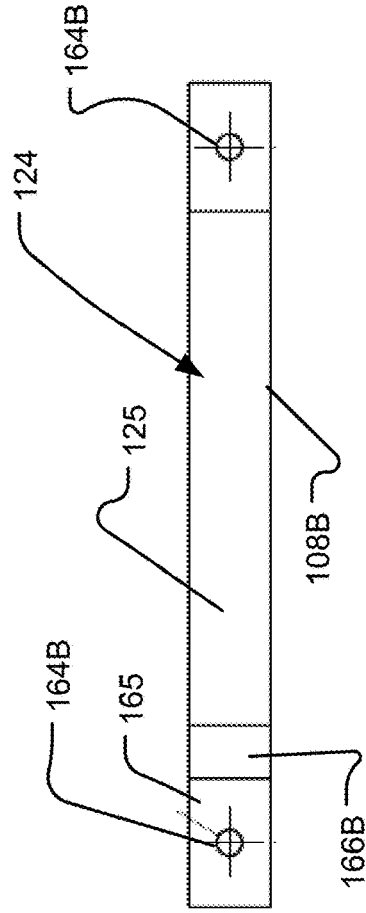
Figure 1M:
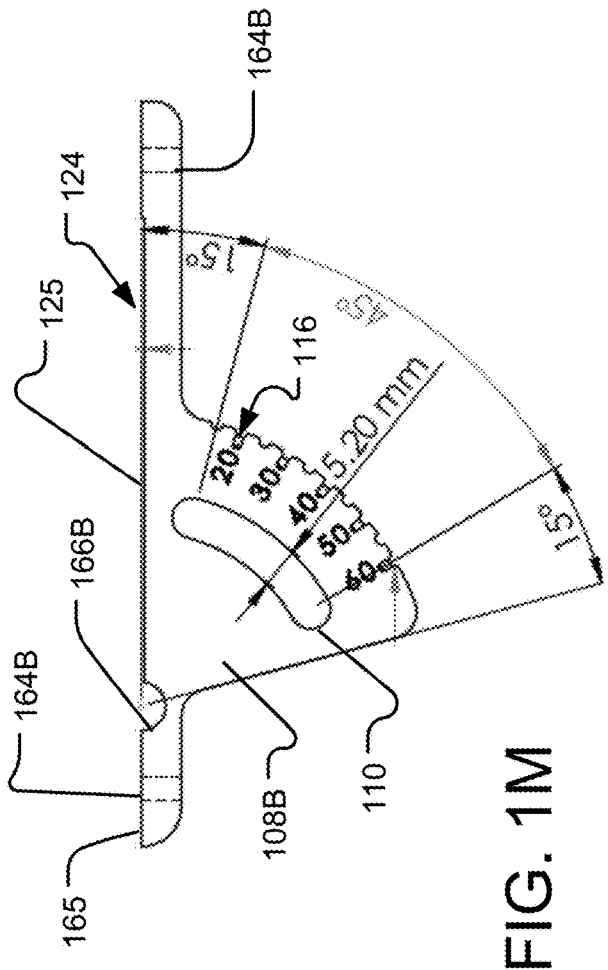
Figure 1N:
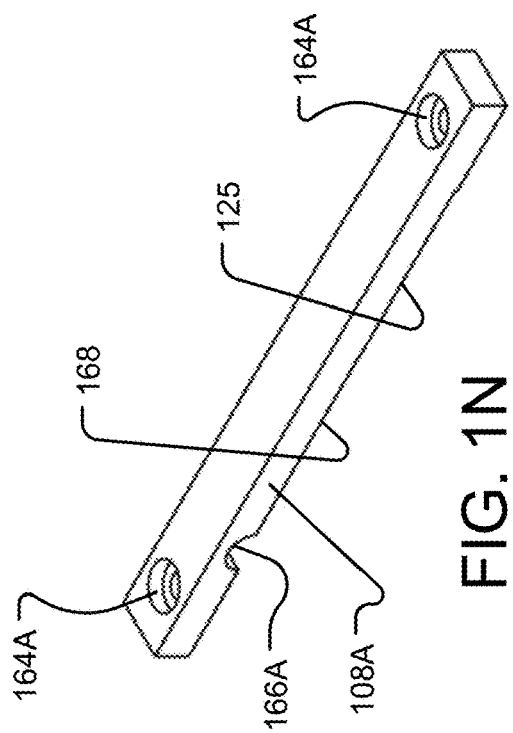
FIGS. 1N-1P are, respectively, an isometric view, a top view, and a side view of the upper part of the cutting guide of the wedge osteotomy device.
Figure 1O:
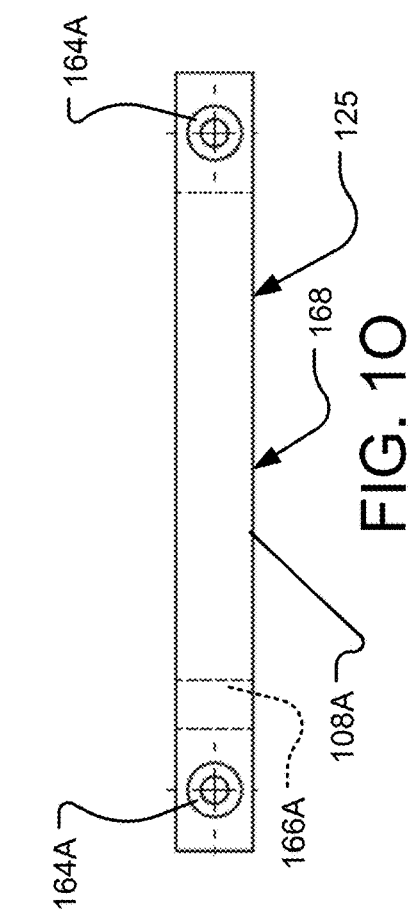
Figure 1P:
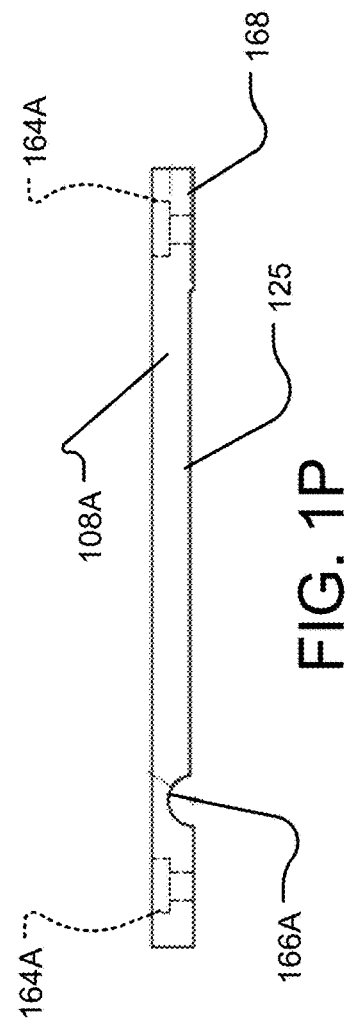

As previously described, the cutting guide 102 may include a single guide body 108 or multiple guide bodies 108A, 108B as shown in the figures. FIGS. 1K-1M depict, respectively, an isometric view, a top view, and a side view of the lower guide body 108B of the cutting guide 102 of the wedge osteotomy device 100. And FIGS. 1N-1P depict, respectively, an isometric view, a top view, and a side view of the upper guide body 108A of the cutting guide 102 of the wedge osteotomy device 100.

With reference to FIGS. 1K-1M, and as stated previously, the lower guide body 108B may include an arcuate slot 110 with an arc defined by a radius to the joint 106. Adjacent the arcuate slot 110 are a series of markers 116 identifying an angular orientation of the cutting guide 102 relative to the base plate 104. The series of markers 116 may include numerical markings indicating the angular orientation in degrees (e.g., 20 degrees, 30 degrees, 40 degrees, 50 degrees, 60 degrees), and/or the series of markers 116 may include notches defined on a front surface of the cutting guide 102. The angular orientation may be determined by where the thumb-screw 112 (as seen in FIGS. 1A and 1B) is positioned relative to the series of markers 116. Thus, when the thumb-screw 112 is tightened against a marker 116 showing "30", the base plate 104 and the cutting slot 124 are 30 degrees apart from each other.

The upper and lower guide bodies 108A, 108B may be secured together via a pair of threaded members 118 that extend through threaded openings 164A, 164B in the upper and lower guide bodies 108A, 108B, respectively. The pair of threaded members 118 may couple the guide bodies 108A, 108B together on opposite sides of the joint 106 with one near a back side 120 of the guide body 108 and one near the front side 122 of the guide body 108.

The cutting or guiding slot 124 may be defined between the upper and lower guide bodies 108A, 108B. The cutting slot 124 includes planar guiding surfaces 125 for guiding a cutting tool (not shown) in making osteotomies to the bone there through. The cutting slot 124 may be partially defined within each of the upper and lower guide bodies 108A, 1086, as seen in the figures, or may be defined within one of the upper and lower guide bodies 108A, 108B only. As seen in FIGS. 1K-1M, the cutting slot 124 is partially defined on a top surface 165 of the lower guide body 108B. And as seen in FIGS. 1N-1P, the cutting slot 124 is partially defined on a bottom surface 168 of the upper guide body 108A.

As seen in FIGS. 1K-1M, a lower-half cylindrical opening 1666 is formed on the top surface 166 of the lower guide body 108B. And, as seen in FIGS. 1N-1P, an upper-half cylindrical opening 166A is formed on a bottom surface 168 of the upper guide body 108A. Together, the upper- and lower-half cylindrical openings 166A, 1666 form a three-hundred degree cylindrical opening that forms part of the joint 106 with the shaft 136 of the base plate 104. Thus, the wedge osteotomy device 100 may be described as including a joint 106 formed of a shaft 136 rotatably coupled to an opening 166. And while the shaft 136 is included on the base plate 104 and the opening 166 is formed within the guide body 108, the shaft 136 may be included on the guide body 108 and the opening 166 may be included on the base plate 104.

D. Wedge Osteotomy Device as Assembled

Figure 1Q:
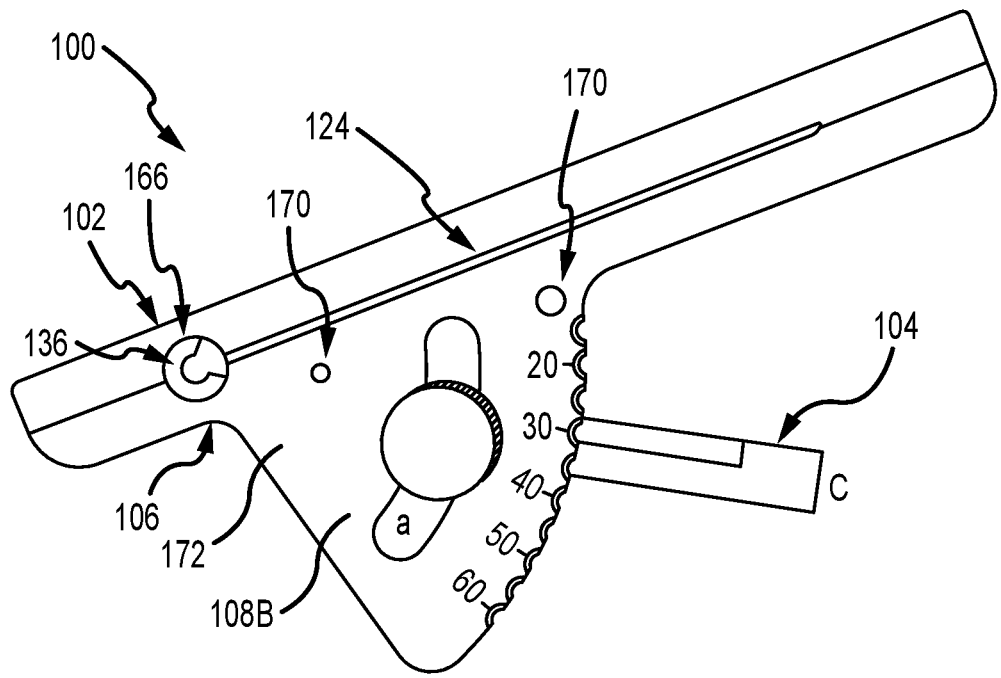
FIGS. 1Q and 1R are, respectively, first and second side views of a wedge osteotomy device.
Figure 1R:
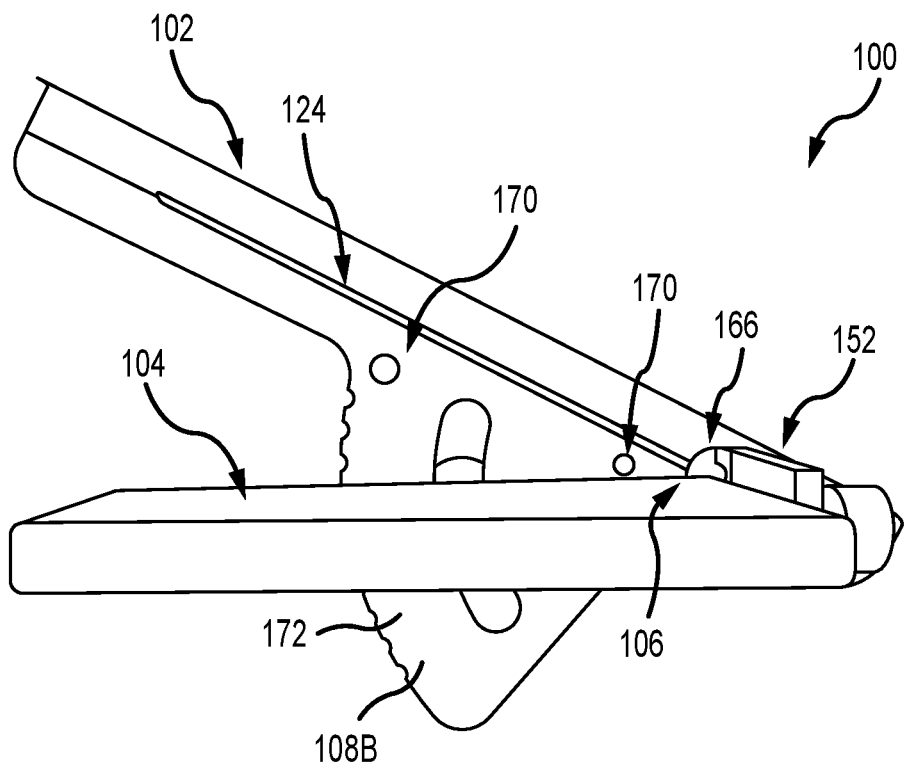

FIGS. 1Q and 1R are, respectively, first and second side views of a wedge osteotomy device 100. The device 100 shown in FIGS. 1Q-1R is the same as previously shown and described except the present device 100 includes a pair of anchoring holes 170 extending through the cutting guide 102. More particularly, the anchoring holes 170 extend through the side surfaces 172 of the lower guide body 108B. As seen in the figures, one of the anchoring holes 170 may be larger than the other so as to accommodate a smaller anchor near the joint 106 and a larger anchor farther from the joint 106. The anchoring holes 170 may be used to guide anchors and/or K-wires into the bone after a first osteotomy is made to the bones, but prior to performing the wedge-resection with the device 100. It is noted that in the case of a wedge-resection with an angular orientation of less than a certain degree, the anchoring hole 170 farthest from the joint 106 may be utilized, as the anchoring hole 170 closer to the joint 106 may be obscured or blocked from use. This may function as a safety since as the angular orientation decreases, there is less bone in which to fasten an anchor. State differently, the device 100 permits the use of multiple anchoring holes 170 in certain angular orientations of the base plate 104 relative to the cutting guide 102 where a sufficient amount of bone is present; but the device 100 only permits a single anchoring hole 170 when the angular orientation is decreased to a certain point where enough bone is present for only a single anchor.

It can be seen in FIGS. 1Q and 1R that the cutting slot 124 extends into the opening 166 of the joint 106 and into the opening of the shaft 136. As seen in these figures, the shaft 136 may be a hollow cylinder. In this way, a cutting tool (not shown) may be guided by the cutting slot 124 all the way to the central axis 144 of the shaft 136 to cut the complete bone, which may be positioned against the blade guard 152. Without cutting to the central axis 144, a portion of the bone may require a finishing cut after the wedge-resection.

II. Method of Using the Wedge Osteotomy Device

Figure 1S:
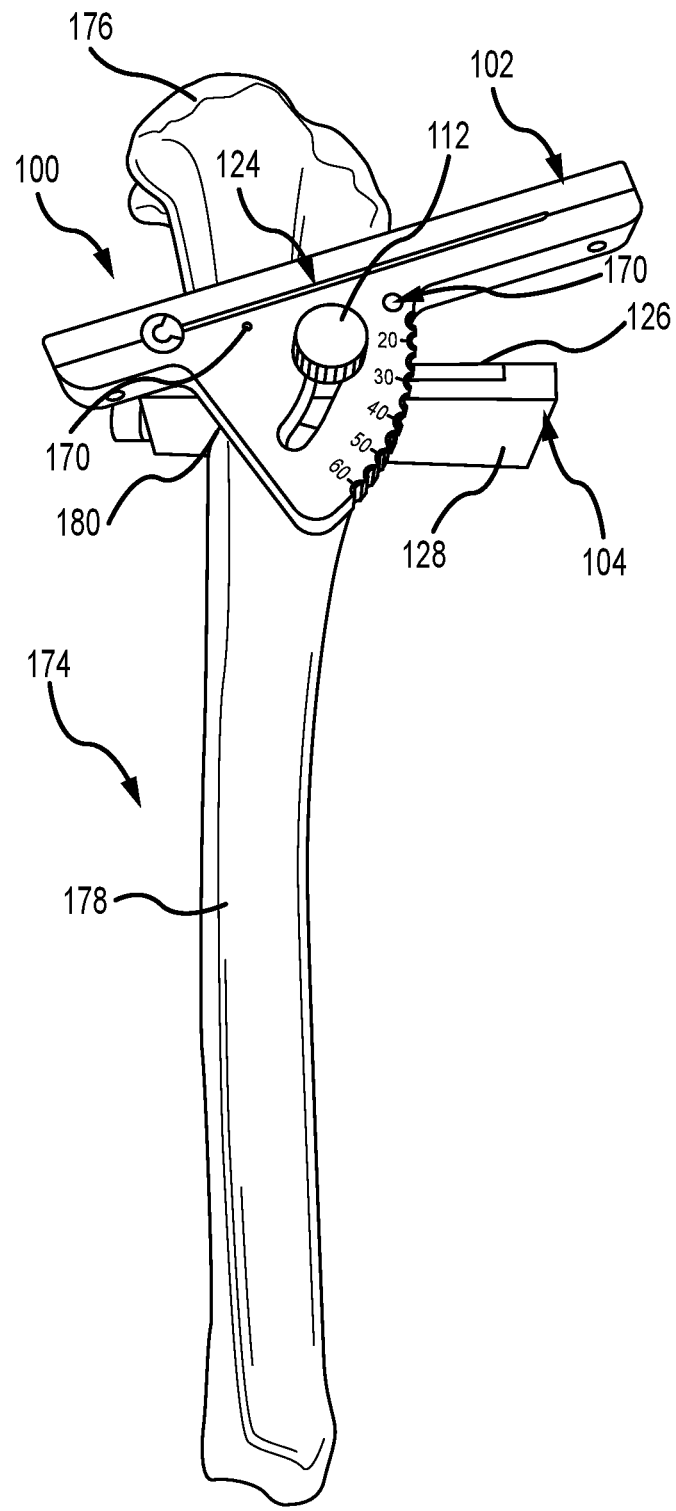
FIGS. 1S and 1T are, respectively, a side view and a top view of a wedge osteotomy device in use on a bone.
Figure 1T:
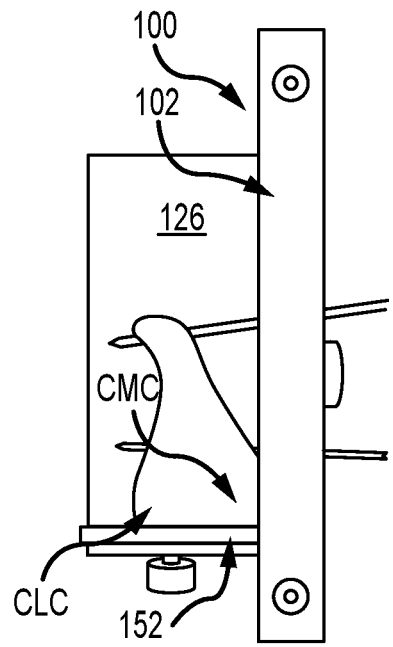
Figure 1U:
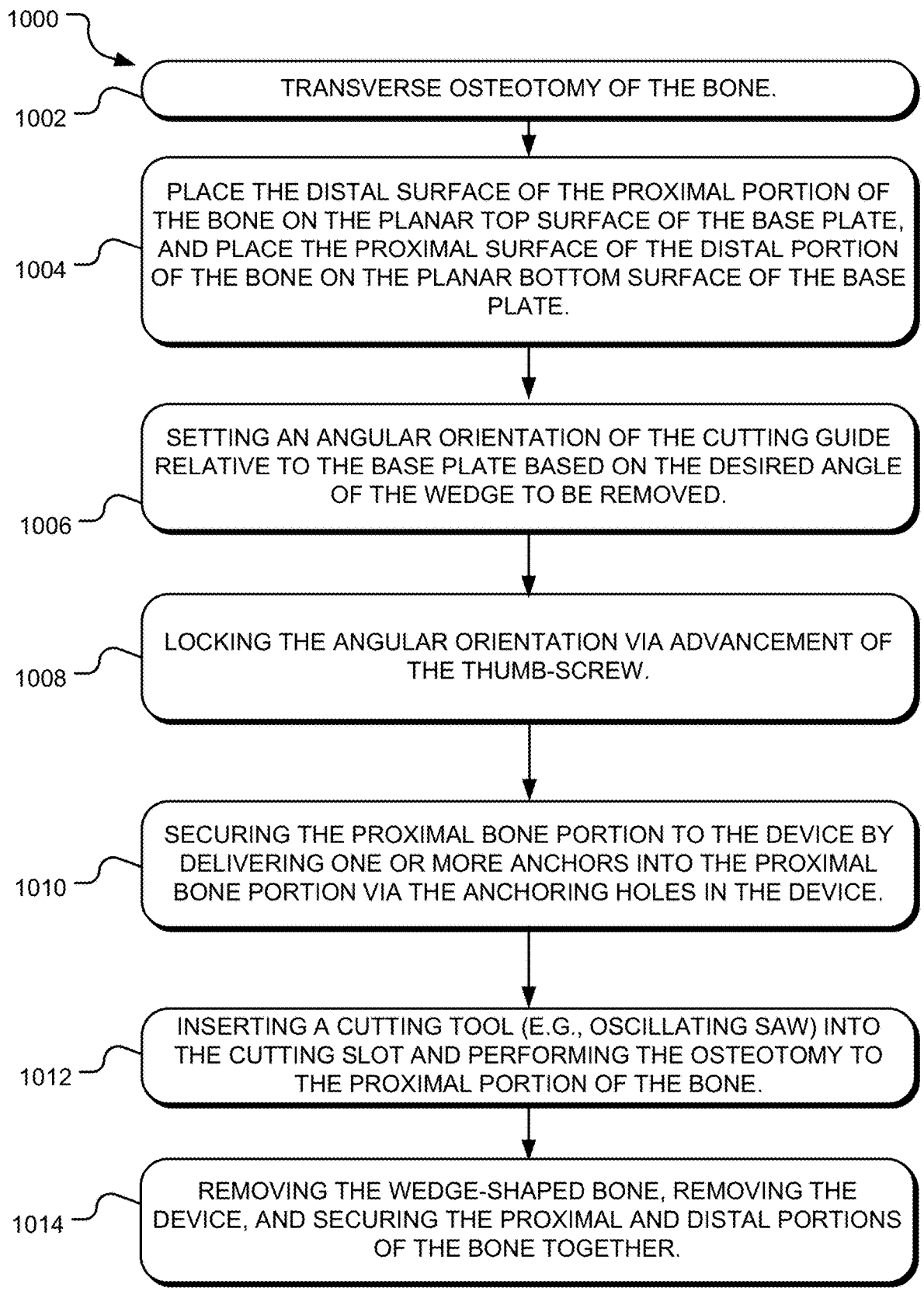
FIG. 1U is a flowchart showing exemplary steps in a method of using the wedge osteotomy device.

The following will describe an exemplary method 1000 of using the wedge osteotomy device 100 with reference to the flow chart of FIG. 1U and the illustrations in FIGS. 1S-1T of the wedge osteotomy device 100 positioned on a bone 174 (e.g., canine tibia) after a transverse osteotomy of the bone 174 was performed. To begin, the method 1000 of FIG. 1U may include, at step 1002, performing a transverse osteotomy of the bone 174, as seen by line 180 in FIG. 1S. The transverse osteotomy may be generally transverse to a longitudinal axis of the bone 174 or generally along the transverse axis of the bone 174. The osteotomy may be according to a pre-operatively planned position and orientation. The transverse osteotomy may be performed by any known methods in the art.

The transverse osteotomy forms two bone portions: a proximal portion 176 having distal surface (not seen in FIG. 1S); and a distal portion 178 having a proximal surface (not seen in FIG. 1S) at the transverse line 180. Next, at step 1004, the method 1000 may include placing the distal surface of the proximal portion 176 of the bone 174 on the planar top surface 126 of the base plate 104, and placing the proximal surface of the distal portion 178 of the bone 174 on the planar bottom surface 128 of the base plate 104. The step 1004 may also include placing an the caudomedial cortex CMC and the caudolateral cortex CLC of the bone 174 against the blade guard 152 coupled to the base plate 104, as seen in FIG. 1T. The method 1000 may next include the step 1006 of setting an angular orientation of the cutting guide 102 relative to the base plate 104. The angular orientation may be determined pre-operatively to correct a certain limb deformity, or otherwise. The angular orientation may, for example, be an angular degree such as 20 degrees, 30 degrees, 40 degrees, 50 degrees, or 60 degrees, among others.

Step 1008 may include locking the angular orientation by advancing the thumb-screw 112. Step 1010 may include delivering one or more anchors into the anchoring holes 170 of the device 100. In the case where both anchoring holes 170 are available based on the particular angular orientation, two anchors may be delivered. In the case, where only a single anchoring hole 170 is available based on a smaller angular orientation, a single anchor may be delivered. As seen in FIG. 1T, the anchoring holes 170 may be non-parallel to each other. That is, the anchoring holes 170 may be angled towards each other. Additionally or alternatively, the anchoring holes 170 may be oriented parallel to each other.

Step 1012 may include inserting a cutting tool into the cutting slot 124 of the cutting guide 102 and resecting the proximal portion 176 of the bone 174. Step 1014 may include removing the wedge-shaped bone of the proximal portion 176, removing the device 100 from the bone 174, and securing the proximal portion 176 and the distal portion 178 together.

Since the base plate 104 and the cutting slot 124 are oriented parallel to each other, in at least one plane, the wedge-resection to the bone, performed at step 1012, is oriented parallel to the transverse osteotomy, performed at step 1002. And since the transverse osteotomy and the wedge-resection meet at the central axis 144 defined by the intersection of the blade guard 152 and the top surface 126 of the base plate 104, the cut height and angle associated with the caudomedial cortex and the caudolateral cortex are the same.

III. Fixed Angle Wedge Osteotomy Device

Figure 2A:
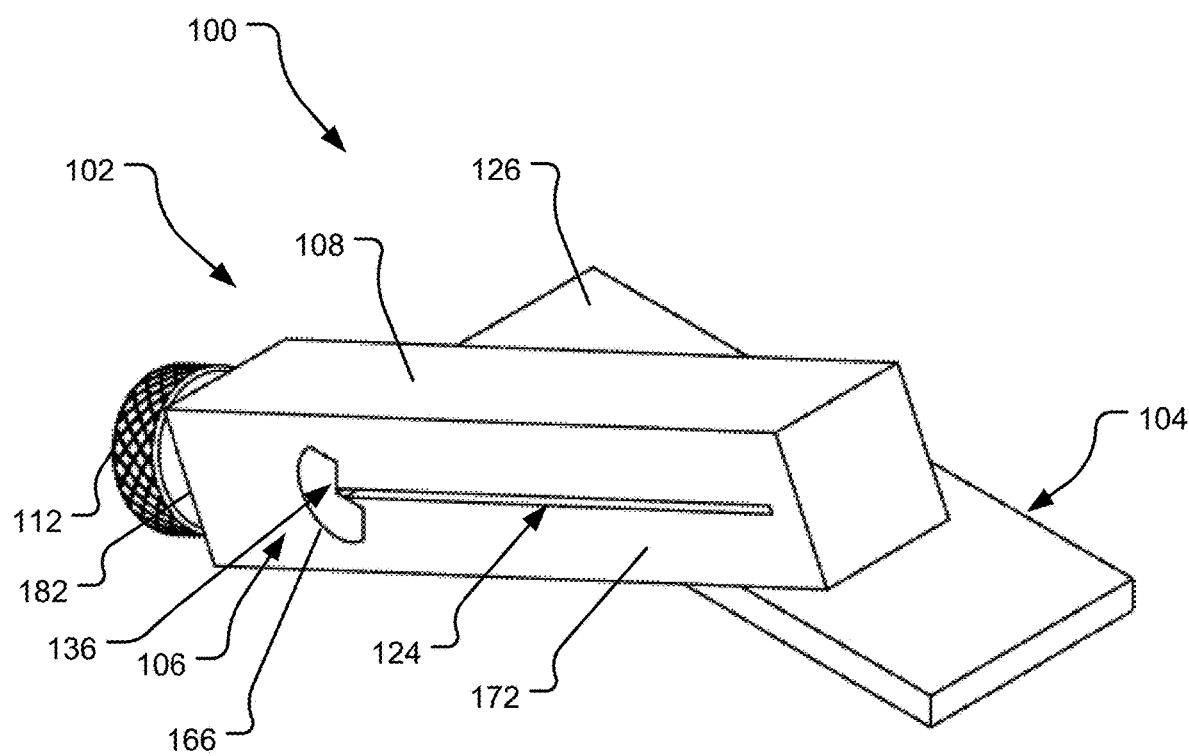
FIGS. 2A-2C are, respectively, an isometric view, a top view, and a side view of a wedge osteotomy device in a second instance.
Figure 2B:
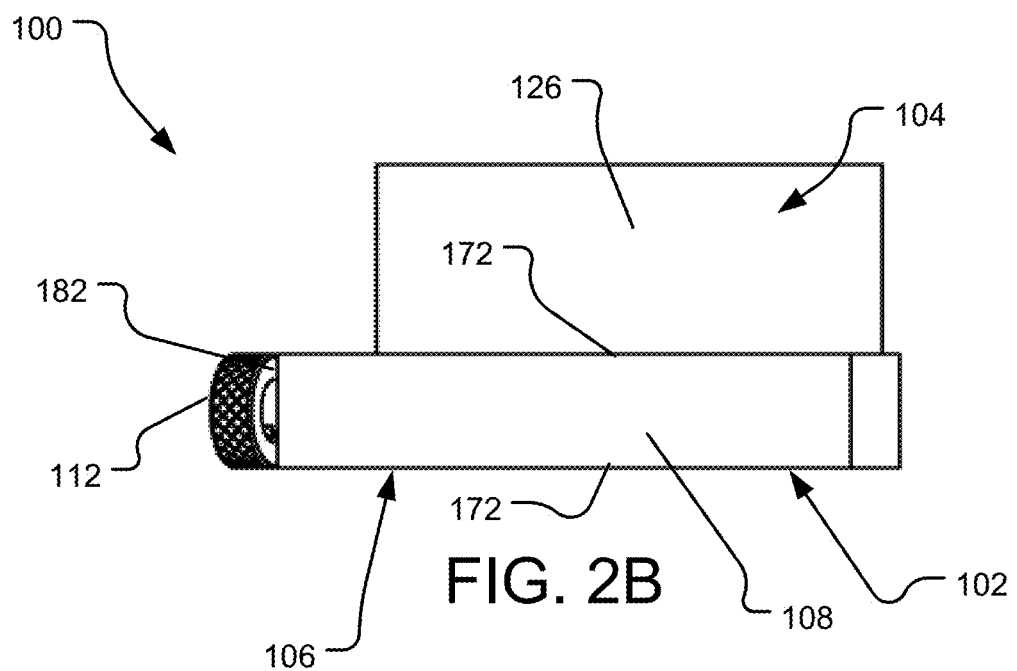
Figure 2C:
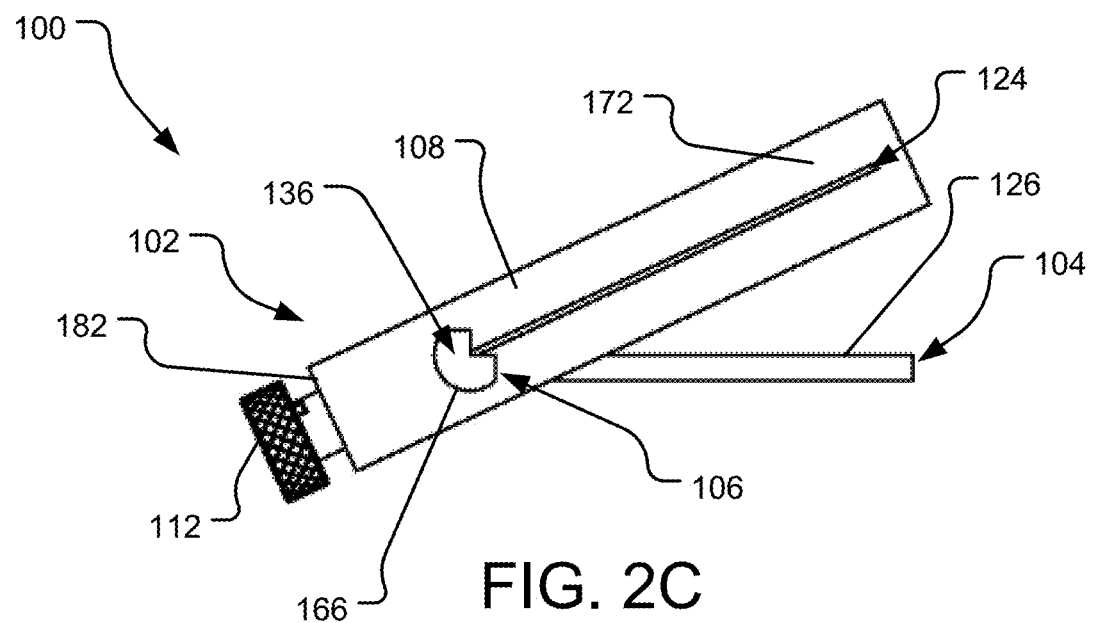

FIGS. 2A-2C depict various view of a fixed angle wedge osteotomy device 100. More particular, FIGS. 2A-2C are, respectively, an isometric view, a top view, and a side view of the fixed angle wedge osteotomy device 100. As seen in the figures, the device 100 may include a cutting guide 102 and a base plate 104 coupled together via a joint 106. The cutting guide 102 may include a guide body 108 having a cutting slot 124 extending through opposite sides 172 thereof. The cutting slot 124 intersects an opening 166 that is partially cylindrical, but not fully cylindrical. The opening 166 forms a first part of the joint 106.

The second part of the joint 106 may be from a shaft 136 extending off of the base plate 104. The shaft 136 may be similarly as described with reference to the shaft 136 shown in FIGS. 1C-1F, among others. The wedge osteotomy device 100 of FIGS. 2A-2C may additionally include a thumb-screw 112 extending through a bore 184 (as seen by the broken lines in FIGS. 2E-2G) in a back surface 182 of the guide body 108. The thumb-screw 112 may be tightened so as to contact the shaft 136 of the base plate 104. In this way, the cutting guide 102 may be secured to the base plate 104 via tightening of the thumb-screw 112.

Figure 2D:
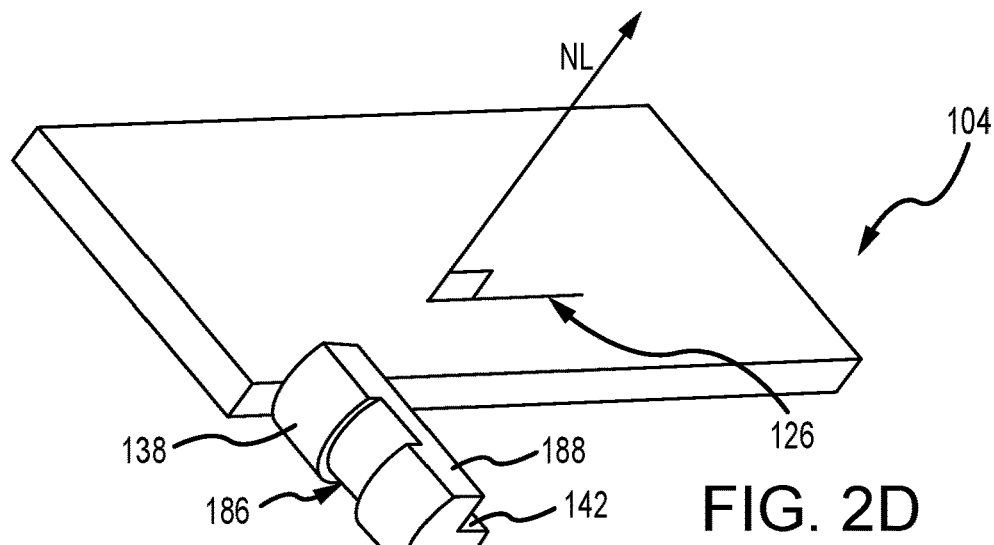
FIG. 2D is an isometric view of a base plate.

As seen in FIG. 2D, which is an isometric view of the base plate 104, the shaft 136 includes a recess 186 defined on the outer cylindrical surface 138. In this way, the thumb-screw 112 may contact the recess 186 when it extends through the bore 184 of the guide body 108, and prevent the shaft 136 from being removed from the opening 166 of the guide body 108 by the sidewalls formed by the recess 186. In this way, the thumb-screw 112 secures or otherwise couples the base plate 104 and the cutting guide 102 together.

The cutting guide 102 in the present instance may be non-adjustable or fixed relative to the base plate 102. That is, the cutting slot 124 may be at a fixed angle relative to the top surface 126 of the base plate 104 when the cutting guide 102 is coupled to the base plate 104. While the cutting guide 102 may be non-adjustable, the device 100 may include multiple cutting guides 102, each with a different angled cut when coupled to the base plate 104. To that end, FIGS. 2E-2G show, respectively, side views of a 25 degree, 40 degree, and 70 degree cutting guide 102.

Figure 2E:
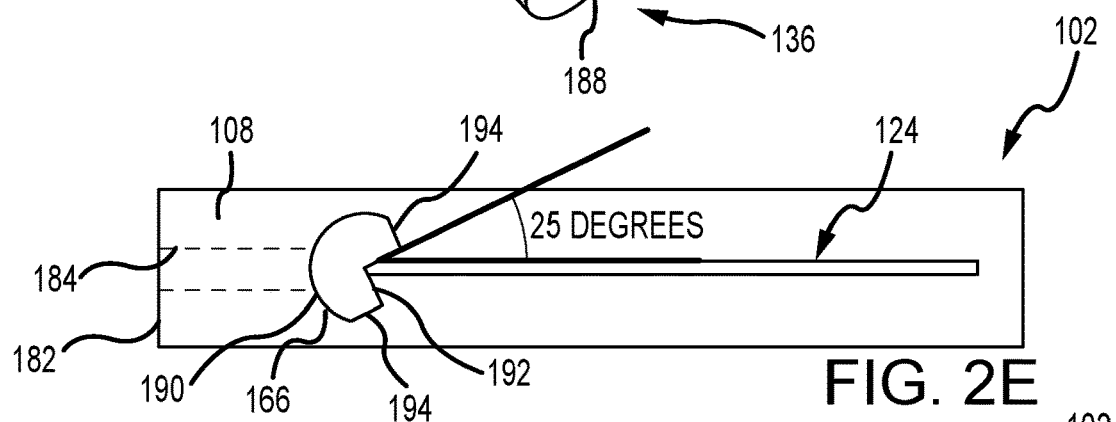
FIGS. 2E-2G are, respectively, side views of a 25 degree, 40 degree, and 70 degree cutting guide.
Figure 2F:
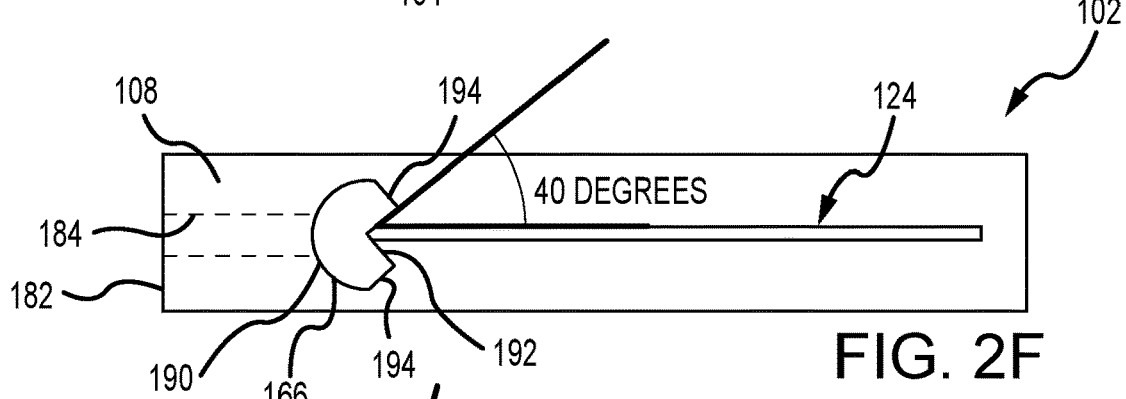
Figure 2G:
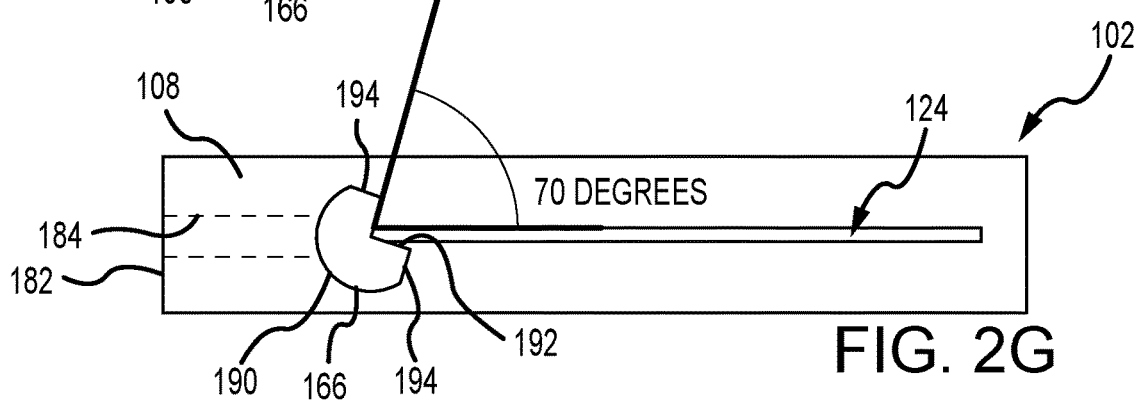

As seen in FIGS. 2E-2G, the opening 166 in the guide body 108 is keyed to the shape of the shaft 136 such that the guide body 108 is non-rotational relative to the base plate 104 when they are coupled together. More specifically, the shaft 136 includes a partial cylindrical surface 138, a pair of planar inner surfaces 142 meeting in the center of the shaft 136, and a pair of planar surfaces 188 notched from the partial cylindrical surface 138. The opening 166 includes corresponding surfaces including a partial cylindrical surface 190, a pair of planar inner surface 192 meeting at a right angle, and a pair of notched surface 194.

When the shaft 136 is received in the opening 166 of the cutting guide 102 of FIG. 2E, the cutting slot 124 makes an angle of 25 degrees with a normal line NL to the top surface 126 of the base plate 104. This device may be used in a surgical procedure where the wedge-cut is desired to be 65 degrees from the transverse cut. In another instance, when the shaft 136 is received in the opening 166 of the cutting guide 102 of FIG. 2F, the cutting slot 124 makes an angle of 40 degrees with a normal line NL to the top surface 126 of the base plate 104. This device may be used in a surgical procedure where the wedge-cut is desired to be 50 degrees from the transverse cut. In another instance, when the shaft 136 is received in the opening 166 of the cutting guide 102 of FIG. 2G, the cutting slot 124 makes an angle of 70 degrees with a normal line NL to the top surface 126 of the base plate 104. This device may be used in a surgical procedure where the wedge-cut is desired to be 20 degrees from the transverse cut. The angles of the cutting slot 124 in FIGS. 2E-2G are exemplary and may include different angles without limitation.

Additionally or alternatively, the device 100 may include a single cutting guide 102 and multiple base plates 104 with each base plate 104 having a different orientation of the shaft 136 to facilitate different angled cuts between the cutting slot 124 of the guide 102 and the base plate 104. In certain instances, the wedge osteotomy device 100 may be part of a kit including a base plate 104 and one or more cutting guides 102. The kit may include sterile packaging and instructions for using the device 100.

IV. Wedge Osteotomy Device with Full Rotational Capabilities

Figure 3:
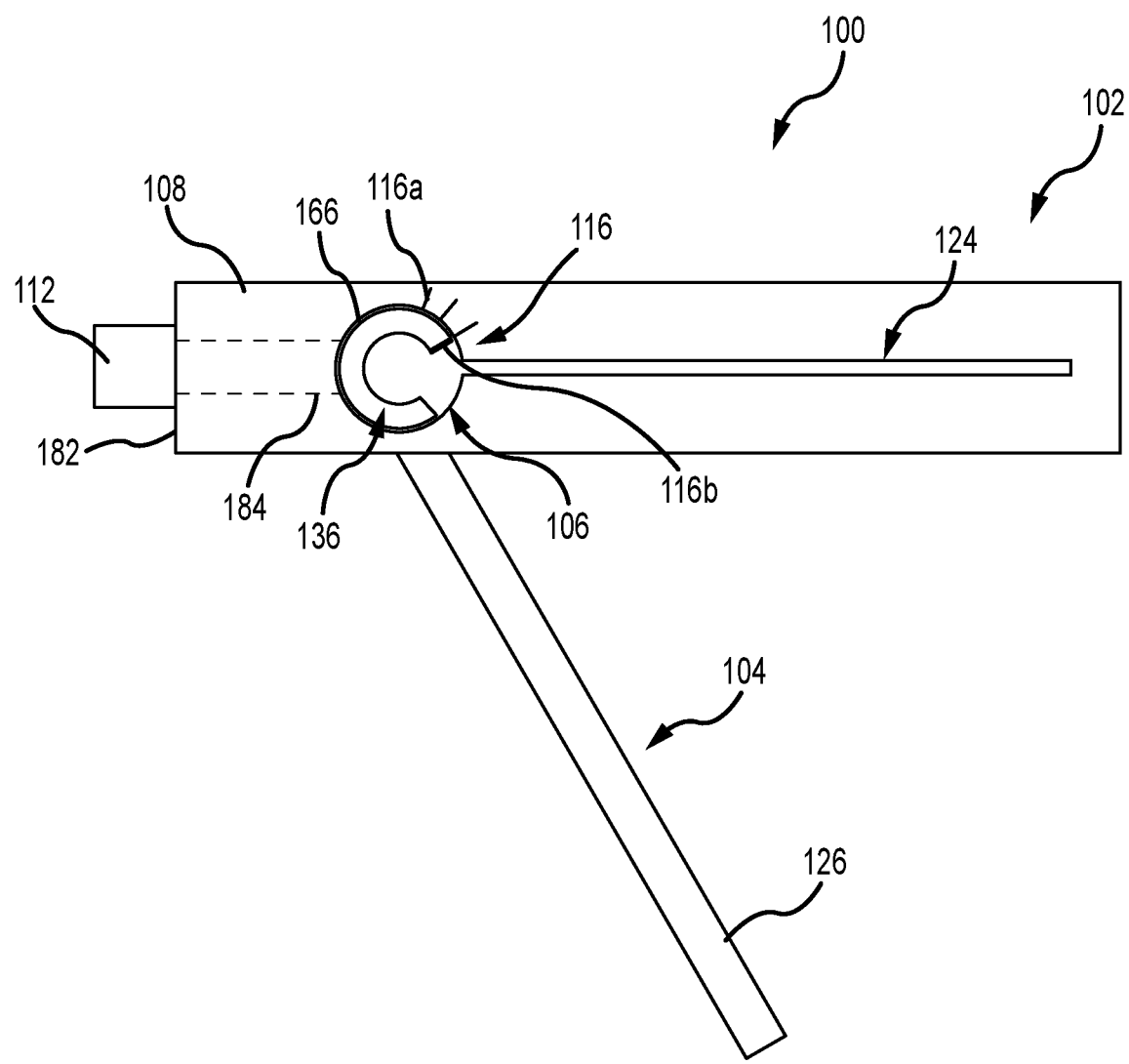
FIG. 3 is a side view of a wedge osteotomy device with rotational locking control.

FIG. 3 depicts a side view of a wedge osteotomy device 100 including substantially the same cutting guide 102 and base plate 104 of FIGS. 2A-2C, except the cutting guide 102 is rotational relative to the base plate 104. As seen in the figure, the opening 166 in the guide body 108 is a full, three hundred sixty degree cylindrical through-hole. The opening 166 may receive a cylindrical shaft 136 of the base plate 104 therein for forming the joint 106. In this way, the shaft 136 can rotate within the opening 166 of the guide body 108 up to three hundred sixty degrees. As seen in the figure, the device 100 may include markers 116 for identifying an angular orientation of the cutting slot 124 relative to the top surface 126 of the base plate 104. As an example, the guide body 108 may include a series of markers 116a and the shaft 136 may include a single marker 116b. The cutting guide 102 may be rotated relative to the base plate 104, and the single marker 116b on the shaft 136 may be aligned collinear to one of the markers 116a on the guide body 108. The markers 116a may be labeled with degrees such as ten degrees, fifteen degrees, twenty degrees, twenty-five degrees, thirty degrees, thirty-five degrees, forty degrees, and seventy degrees, among other angular designations. In certain instances, the markers 116a may be labeled in single degree increments or five degree increments, for example, to provide a range of adjustment opportunities.

Once the desired markers 116a, 116b are aligned for a desired osteotomy, the thumb-screw 112 extending through the bore 184 and through the back surface 182 of the guide body 108 may be tightened so as to contact the shaft 136. Once sufficiently tightened against the shaft 136, the base plate 104 is then secured or locked in the desired angular orientation relative to the cutting guide 102.

As seen in FIG. 3, the shaft 136 may include a cylindrical wall with a central opening at the axis of rotation. The cylindrical wall of the shaft 136 may define an opening into the central opening for receiving a cutting tool to cut all the way to the axis of rotation. The size of the opening in the cylindrical wall may be large enough to permit the specific osteotomies defined by the series of markers 116. Alternatively, the shaft 136 may be a full cylinder so as to permit osteotomies of any angular orientation.

It is noted that features from the various embodiments may be combined with features from other embodiments without departing from the scope of the present disclosure. Although various representative embodiments have been described above with a certain degree of particularity, those skilled in the art could make numerous alterations to the disclosed embodiments without departing from the spirit or scope of the inventive subject matter set forth in the specification. All directional references (e.g., top, bottom, front, back) are only used for identification purposes to aid the reader's understanding of the embodiments of the present disclosure, and do not create limitations, particularly as to the position, orientation, or use of the embodiments unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In methodologies directly or indirectly set forth herein, various steps and operations are described in one possible order of operation, but those skilled in the art will recognize that steps and operations may be rearranged, replaced, or eliminated without necessarily departing from the spirit and scope of the present disclosure. It is intended that all matter contained in the above description or shown in the accompanying drawings shall be interpreted as illustrative only and not limiting. Changes in detail or structure may be made without departing from the spirit of the disclosure as defined in the appended claims.

What is claimed is:

1. A wedge osteotomy device comprising:
a cutting guide coupled to a base plate via a joint, the cutting guide configured to pivot relative to the base plate about a pivot axis extending through the joint, the cutting guide comprising a guide body including a cutting slot extending through the guide body, an arcuate slot extending through the guide body and defining a radius to the joint, and a plurality of markers on the guide body identifying a position of the cutting guide relative to the base plate, the base plate comprising planar top and bottom surfaces, wherein the guide body further includes a cylindrical bore defining a first portion of the joint and extending through the guide body, the cutting slot intersecting the cylindrical bore.

2. The wedge osteotomy device of claim 1, further comprising a blade guard coupled to the base plate and comprising a surface perpendicular to the planar top surface.

3. The wedge osteotomy device of claim 2, wherein the pivot axis is at the intersection of the surface of the blade guard and the planar top surface of the base plate.

4. The wedge osteotomy device of claim 1, wherein the cutting slot is a planar cutting slot.

5. The wedge osteotomy device of claim 1, wherein the position is an angular position.

6. The wedge osteotomy device of claim 1, wherein the base plate further comprises a shaft extending from a side surface of the base plate, the shaft being receivable within the cylindrical bore and defining a second portion of the joint.

7. The wedge osteotomy device of claim 6, wherein the shaft comprises a partial cylinder having an opened segment extending longitudinally on the shaft, the partial cylinder including a planar first surface coplanar with the planar top surface of the base plate.

8. The wedge osteotomy device of claim 7, the partial cylinder including a planar second surface perpendicular to the planar first surface.

9. The wedge osteotomy device of claim 1, further comprising a thumb-screw securable to the base plate through the arcuate slot.

10. The wedge osteotomy device of claim 1, wherein the guide body further includes at least one anchor bores extending through the guide body, the at least one anchor bores positioned below the cutting slot.

11. A wedge osteotomy device comprising:
a cutting guide coupled to a base plate via a joint, the cutting guide configured to pivot relative to the base plate about a pivot axis extending through the joint, the cutting guide comprising a guide body including a cutting slot extending through the guide body, an arcuate slot extending through the guide body and defining a radius to the joint, and a plurality of markers on the guide body identifying a position of the cutting guide relative to the base plate, the base plate comprising planar top and bottom surfaces, wherein the cutting slot intersects the pivot axis.

12. The wedge osteotomy device of claim 11, further comprising a blade guard coupled to the base plate and comprising a surface perpendicular to the planar top surface.

13. The wedge osteotomy device of claim 12, wherein the pivot axis is at the intersection of the surface of the blade guard and the planar top surface of the base plate.

14. The wedge osteotomy device of claim 11, wherein the cutting slot is a planar cutting slot.

15. The wedge osteotomy device of claim 11, wherein the position is an angular position.

16. The wedge osteotomy device of claim 11, further comprising a thumb-screw securable to the base plate through the arcuate slot.

17. A wedge osteotomy device comprising:
a cutting guide coupled to a base plate via a joint, the cutting guide configured to pivot relative to the base plate about a pivot axis extending through the joint, the cutting guide comprising a guide body including a cutting slot extending through the guide body, and a bore extending through the guide body and intersecting the cutting slot, the base plate comprising planar top and bottom surfaces and a shaft extending from a side thereof, the shaft being receivable within the bore to form the joint, the shaft comprising a partial cylindrical outer surface, and a side opening extending from the partial cylindrical outer surface to a central axis thereof.

18. The wedge osteotomy device of claim 17, further comprising a thumb-screw rotatably coupled with the guide body and configured to secure the cutting guide in an angular position relative to the base plate.

19. The wedge osteotomy device of claim 17, wherein the shaft further comprises a planar surface coplanar with the planar top surface of the base plate.

20. The wedge osteotomy device of claim 17, wherein the cutting slot extends to the pivot axis through the side opening of the shaft of the base plate.

* * * * *